US00PP23982P2

(12) United States Plant Patent
Kordes

(10) Patent No.: US PP23,982 P2
(45) Date of Patent: Oct. 15, 2013

(54) MINIATURE ROSE PLANT NAMED 'KORPOT019'

(50) Latin Name: *Rosa hybrida*
Varietal Denomination: KORpot019

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 89 days.

(21) Appl. No.: 13/385,492

(22) Filed: Feb. 21, 2012

(51) Int. Cl.
*A01H 5/00* (2006.01)

(52) U.S. Cl.
USPC ..... Plt./118

(58) Field of Classification Search
USPC ..... Plt./118
See application file for complete search history.

(56) References Cited

U.S. PATENT DOCUMENTS

PP15,240 P3 * 10/2004 Hansen ..... Plt./118
PP20,208 P2 * 8/2009 Kordes ..... Plt./118

OTHER PUBLICATIONS

Pluto UPOV QZ Results for 'KORpot019' Apr. 15, 2012.*

* cited by examiner

*Primary Examiner* — Wendy C Haas

(57) ABSTRACT

A new and distinct variety of rose with long lasting, novel yellow flowers, and attractive foliage with very good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot019'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2008. The crossing was between an 'un-named seedling', the seed parent, and another 'un-named seedling', the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot019'.

SUMMARY OF THE INVENTION

The new rose plant may be distinguished from its seed parent, an 'un-named seedling', by the following combination of characteristics:

1. 'KORpot019' has double yellow flowers whereas the seed parent has very double yellow flowers with pink edges.
2. 'KORpot019' has a compact habit, whereas the seed parent has a tall habit.

The new rose plant may be distinguished from its pollen parent, an 'un-named seedling', by the following combination of characteristics:

1. 'KORpot019' has medium sized double flowers, whereas the pollen parent has small semi-double flowers.
2. 'KORpot019' has above average disease resistance, whereas the pollen parent has average disease resistance.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpot019' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot019' was selected in May, 2009 from the seedling beds to be asexually propagated for further evaluation. The first asexual propagation of 'KORpot019' was done by rooting cuttings in June, 2009 at the inventor's nursery in Offenseth-Sparrieshoop, Germany.

This initial and other subsequent propagations conducted in controlled environments demonstrate that 'KORpot019' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORpot019'.

DETAILED BOTANICAL DESCRIPTION

The following is a description of 'KORpot019', as observed growing in January, 2012 in a nursery in Jackson County, Oreg., on plants 10 months of age. Color references are made using The Royal Horticultural Society (London, England) Colour Chart, 2001 except where common terms of color are used.

For a comparison, several physical characteristics of the rose variety 'KORspunty', a rose variety from the same inventor described and illustrated in U.S. Plant Pat. No. 17,402 and issued on Feb. 6, 2007 are compared to 'KORpot019' in Chart 1.

CHART 1

| Characteristic | 'KORpot019' | 'KORspunty' |
|---|---|---|
| General tonality | Yellow-Orange Group 16B | Yellow Group 9B |
| Petal count | 35-40 | 50-60 |
| Pistil count | Approximately 25 | 35-45 |

Parents:

*Seed parent*.—'Un-named seedling'.

*Pollen parent*.—'Un-named seedling'.

Classification:

*Botanical classification*.—*Rosa hybrida* 'KORpot019'.

*Commercial classification*.—Miniature rose.

FLOWER AND FLOWER BUD

*Blooming habit*.—Recurrent.

*Flower bud*.—Size: Upon opening, 35 mm in length from base of receptacle to distal end of bud and 23 mm diameter at its widest point. Bud form: Long. Pointed ovoid. Bud color: As sepals first unfold, bud color is Yellow-Orange Group 22A and Yellow-Orange Group 22B. When ¼ open, the upper surface of petals is Yellow-Orange Group 14A, and the lower surface is Yellow Group 13B. Guard Petals are Yellow-Orange Group 19A and Yellow-Orange Group 19B, with a basal zone of Yellow-Green Group 146C and red intonation of Greyed-Red Group 180A. Sepals: Color: Upper surface Yellow-Green Group 146D. Lower surface Yellow-Green Group 146A. Size: Average 26 mm (l)×6 mm (w). Shape: Very weak foliaceous appendages on 0 to 2 of the 5 sepals. Apex: Apiculate. Base: Flat at union with receptacle. Quantity: Five. Surface texture: Upper side: Pubescent. Lower surface: Smooth with numerous stipitate glands. Margins: Pubescent with limited stipitate glands.

*Receptacle*.—Surface: Smooth with a few stipitate glands near top. Color: Yellow-Green Group 146C with intonations of Greyed-Orange Group 175A. Shape: Urn-shaped. Size: 9 mm (h)×9 mm (w).

*Peduncle*.—Surface: With fine hairs. Length: 60 to 65 mm average length. Diameter: 3 to 4 mm average diameter. Color: Yellow-Green Group N146C and Yellow-Green Group N144A with intonations of Greyed-Red Group 178B. Strength: Strong. Borne: Singularly.

Flower bloom:

*Fragrance*.—Light-moderate.

*Duration*.—On the plant 10 to 12 days. Long lasting. Senesced petals drop away cleanly.

*Size*.—Large for a miniature rose. When open, the average flower diameter is 50 mm and the average flower height is 35 mm.

*Form*.—Shape of flower when viewed from the side: Upon opening, upper part: Flat. Upon opening, lower part: Flattened convex. Open flower, upper part: Flattened to flattened convex. Open flower, lower part: Flattened convex.

Color:

*Upon opening, petals*.—Outermost petals: Outer Side: Yellow-Orange Group 14C, with Yellow-Orange Group 14B at margins. Inner Side: Yellow-Orange Group 14A. Innermost petals: Outer Side: Yellow-Orange Group 14C. Inner Side: Yellow Group 12A.

*Upon opening, basal petal spots*.—Basal petal spot, outermost petals: Outer Side: Green-Yellow Group 1A. Inner Side: None observed. Basal petal spot, innermost petals: Outer Side: None observed. Inner Side: None observed.

*After opening, petals*.—Outermost petals: Outer Side: Yellow-Orange Group 18A. Inner Side: Yellow-Orange Group 15C. Innermost petals: Outer Side: Yellow-Orange Group 21C. Inner Side: Yellow-Orange Group 15B.

*After opening, basal petal spots*.—Basal petal spot, outermost petals: Outer Side: Green-Yellow Group 1C. Inner Side: None observed. Basal petal spot, innermost petals: Outer Side: None observed. Inner Side None observed.

General tonality: On open flower Yellow-Orange Group 16B. No change in the general tonality at the end of the seventh day. Afterwards, general tonality is Yellow-Orange Group 16D.

Petals:

*Petal count*.—Double.

*Average range*.—Approximately 35 to 40 petals under normal conditions.

*Petal reflex*.—Petals reflex slightly.

*Petal edge*.—Entire with a point in the center.

*Petal shape*.—Obovate. Apex shape is round. Shape of base is obtuse.

*Petal size*.—30-35 mm (l) 25-30 mm (w).

*Thickness*.—Thick.

*Petal arrangement*.—Not formal.

Petaloids:

*Petaloid count*.—Average of 6 to 10 per flower.

*Petaloid size*.—Petaloids are 15-25 mm (l) and 8-12 mm (w).

*Petaloid color*.—Color of inner side is Yellow Group 13D. Color of outer side is Yellow-Orange Group 16B.

*Petaloid texture*.—Thick.

*Margins*.—Irregular.

*Petaloid shape*.—Most commonly deltoid, with some petaloids highly irregular. Apex: Oblanceolate. Base: Attenuate.

Reproductive organs:

*Pistils*.—Abundant. Approximately 25 present. Stigmas: Location: Slightly inferior in position to anthers. Color: Yellow-Green Group 150C. Styles: Length: About 5 mm long. Color: Green-Yellow Group 160A.

*Stamens*.—Approximately 60 on average and regularly arranged. Anthers: Size: Average 2-3 mm (l). Pollen: Generally present in limited amounts. Color: Greyed-Orange Group 165B. Filaments: Color: Yellow-Orange Group 17C. Length: 4-6 mm.

THE PLANT

*Growth*.—Moderate.

*Plant habit*.—Upright to bushy habit. When grown as a 10 cm pot plant, the average plant height is 25-30 cm and the average plant width is 12-15 cm.

*Blooming*.—Floriferous.

*Stems*.—Stem color: Young wood: Yellow-Green Group 146A. Older wood: Green Group 137C. Stem surface: Young wood: Smooth. Older wood: Smooth.

*Prickles*.—Present. Incidence: Average of 8 per each 10 cm of stem. Size: Average length: 3-4 mm. Color: Immature prickles: Greyed-Purple Group 185B. Mature prickles: Greyed-Orange Group 166C. Shape: Linear to concave.

*Leaves and leaflets*.—Normally 5 leaflets on normal leaves in middle of the stem. Venation pattern: Pyramidal net pattern. Leaf size: 90-100 mm (l)×40-55 mm (w). Abundance: Average. Texture: Leathery. Upper side of leaflet: Semi-glossy, smooth. Under side of leaflet: Matte, smooth. Color, mature foliage: Upper Leaf Surface: Green Group 137A. Lower Leaf Surface: Green Group 137C. Color, juvenile foliage: Upper Leaf Surface: Green Group 137B. Lower Leaf Surface: Green Group 137C. Anthocyanin intonation: Present. Intonations of Greyed-Purple Group 187B present on leaflet edges and lower side.

*Stipules*.—Size: 5 mm long, 3 mm from distal tip to distal tip. Stipule color: Green Group 137B. Margins: With stipitate glands. Shape: Apex: Apiculate. Base: Slightly winged.

*Petiole*.—Length: Average 12-15 mm. Diameter: Average 1.5 mm. Petiole color: Green Group Green-Yellow Group 144A. Underneath: Smooth with occasional prickles. Margins: With stipitate glands. Anthocyanin: Greyed-Purple Group 183B found on margins. Prickles: Occasional.

*Petiole rachis*.—Length: Average 18-20 mm. Diameter: Average 1 mm. Color: Yellow-Green Group 144B. Margins: With occasional stipitate glands.

*Leaflets*.—Size: Average size of the terminal leaflet is 35-40 mm (l)×20-25 mm (w). Shape: Ovate. Base: Obtuse. Apex: Murconate. Margins: Serrated. Surface: Upper: Moderately glossy. Lower: Matte. Texture: Thin. Arrangement: Odd pinnate Venation Reticulate.

Hips/seed formation: Not observed.

Winter hardiness: Unknown

Disease resistance: Very good average resistance to Powdery mildew (*Sphaerotheca pannosa*), and Botrytis (*Botrytis cinerea*) diseases under normal growing conditions.

I claim:

1. A new and distinct variety of rose plant, as described and illustrated herein.

* * * * *

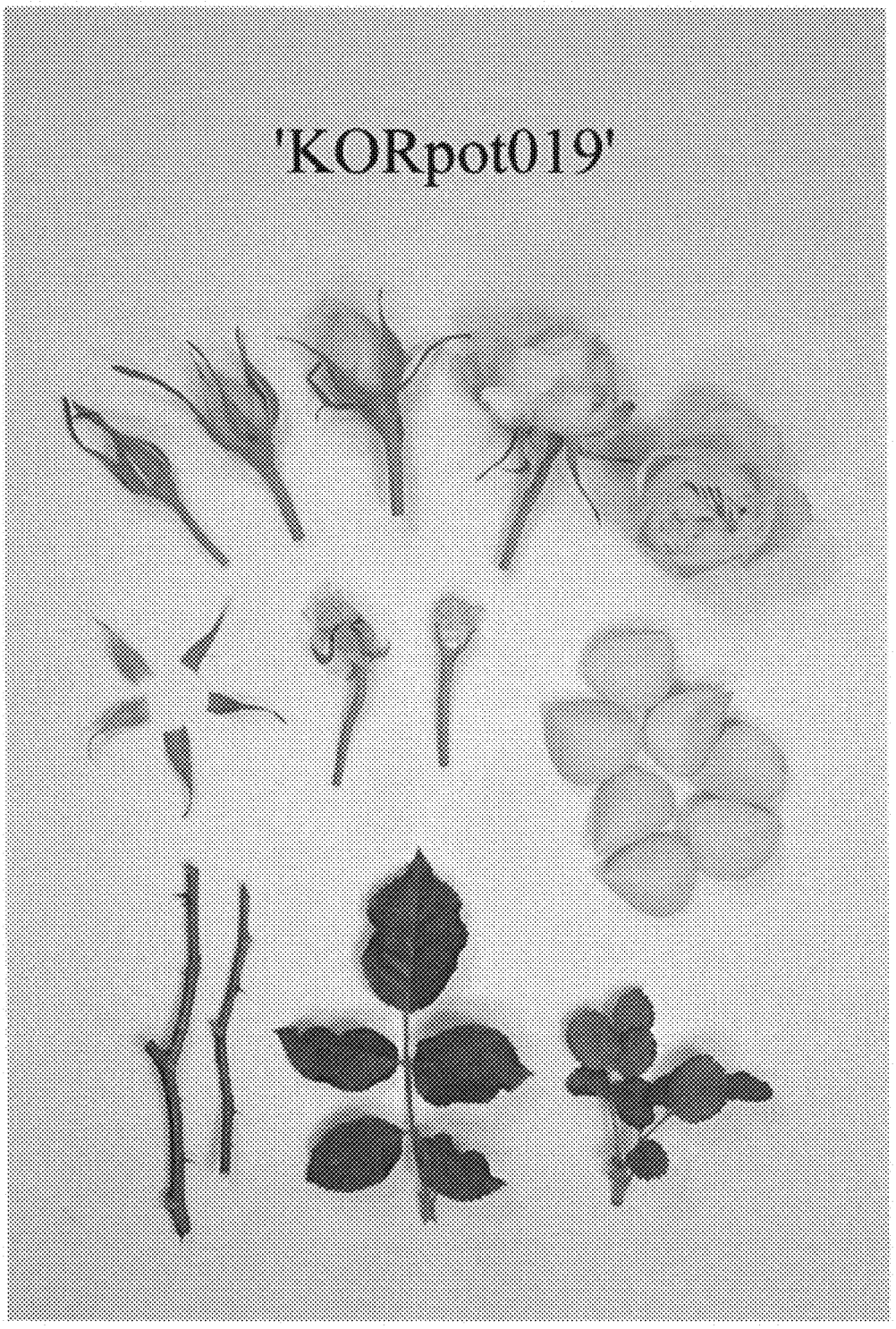
'KORpot019'